United States Patent
Van De Pas et al.

(10) Patent No.: US 11,413,011 B2
(45) Date of Patent: Aug. 16, 2022

(54) ULTRASOUND BASED TRACKING

(71) Applicant: KONINKLIJKE PHILIPS N.V., Eindhoven (NL)

(72) Inventors: Stefan Van De Pas, Herten (NL); Hendrik Roelof Stapert, Rosmalen (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 774 days.

(21) Appl. No.: 16/063,858

(22) PCT Filed: Dec. 13, 2016

(86) PCT No.: PCT/EP2016/080708
§ 371 (c)(1),
(2) Date: Jun. 19, 2018

(87) PCT Pub. No.: WO2017/108490
PCT Pub. Date: Jun. 29, 2017

(65) Prior Publication Data
US 2018/0368807 A1 Dec. 27, 2018

(30) Foreign Application Priority Data
Dec. 22, 2015 (EP) .................................. 15201890

(51) Int. Cl.
*A61B 34/20* (2016.01)
*A61B 8/00* (2006.01)
(Continued)

(52) U.S. Cl.
CPC .......... *A61B 8/4245* (2013.01); *A61B 8/0841* (2013.01); *A61B 8/4254* (2013.01);
(Continued)

(58) Field of Classification Search
CPC ..... A61B 8/4245; A61B 8/4444; A61B 34/20; A61B 8/12; A61B 2034/2063; G01S 5/30
See application file for complete search history.

(56) References Cited

U.S. PATENT DOCUMENTS

| 4,567,896 A | * | 2/1986 | Barnea | ................ | A61B 8/0833 |
| | | | | | 600/443 |
| 5,196,343 A | | 3/1993 | Zerhouni | | |

(Continued)

FOREIGN PATENT DOCUMENTS

| JP | 2011182983 A | 9/2011 |
| WO | 199840760 A1 | 9/1998 |

(Continued)

OTHER PUBLICATIONS

Mung, J. et al "Time of Flight and FMCW Catheter Localization", IEEE International Ultrasonics Symposium Proceedings, pp. 590-593. 2009.

(Continued)

*Primary Examiner* — Jonathan Cwern
*Assistant Examiner* — Amal Aly Farag (57) ABSTRACT

The present invention relates to an ultrasound-based system for localizing a medical device within the field of view of an ultrasound imaging probe. A localization system is provided that includes at least three ultrasound emitters that are arranged on a frame; and a position triangulation unit. The frame is adapted for attachment to an ultrasound imaging probe. The position triangulation unit determines a spatial position of the ultrasound detector relative to the at least three ultrasound emitters based on signals received from an ultrasound detector that is attached to the medical device. The frame includes a detachable reference volume comprising a background volume and an inclusion or void. When the detachable reference volume is attached to the frame and the frame is attached to the ultrasound imaging probe the (Continued)

inclusion or void provides a corresponding image feature within the field of view of the ultrasound imaging probe for use in calibrating the field of view of the ultrasound imaging probe with the coordinate system of the localization system.

12 Claims, 5 Drawing Sheets

(51) Int. Cl.
- *G01S 5/30* (2006.01)
- *A61B 8/08* (2006.01)
- *A61B 90/00* (2016.01)
- *A61B 8/12* (2006.01)
- *G01S 17/48* (2006.01)

(52) U.S. Cl.
CPC ............ *A61B 8/4444* (2013.01); *A61B 34/20* (2016.02); *G01S 5/30* (2013.01); *A61B 8/12* (2013.01); *A61B 8/587* (2013.01); *A61B 2034/2063* (2016.02); *A61B 2090/378* (2016.02); *A61B 2090/3786* (2016.02); *G01S 17/48* (2013.01)

(56) References Cited

U.S. PATENT DOCUMENTS

| | | | |
|---|---|---|---|
| 5,515,853 A | 5/1996 | Smith | |
| 6,216,029 B1 | 4/2001 | Paltieli | |
| 6,338,716 B1* | 1/2002 | Hossack | A61B 8/0833 600/459 |
| 6,719,700 B1 | 4/2004 | Willis | |
| 2003/0122544 A1* | 7/2003 | Parker | G01N 29/30 324/309 |
| 2013/0055788 A1 | 3/2013 | Amit | |
| 2013/0266178 A1 | 10/2013 | Jain | |
| 2014/0043933 A1* | 2/2014 | Belevich | A61B 8/4488 367/11 |
| 2014/0343425 A1 | 11/2014 | Ihnatsenka | |
| 2014/0364719 A1* | 12/2014 | Byrd | A61B 8/54 600/409 |
| 2015/0173723 A1 | 6/2015 | Bates | |
| 2015/0182187 A1 | 7/2015 | Samset | |
| 2016/0033791 A1 | 2/2016 | Kozu | |
| 2016/0331351 A1* | 11/2016 | Guracar | A61B 8/4254 |

FOREIGN PATENT DOCUMENTS

| | | |
|---|---|---|
| WO | 2012172458 A1 | 12/2012 |
| WO | 2014026185 A1 | 2/2014 |
| WO | 2015155645 A1 | 10/2015 |

OTHER PUBLICATIONS

Vilkomerson, D. et al "A System for Ultrasonics Beacon-Guidance of Catheters and Other Minimally-Invasive Medical Devices", IEEE Transactions on Ultrasonics, Ferroelectrics and Frequency Control, vol. 44, No. 1, Jan. 1997.

* cited by examiner

ULTRASOUND BASED TRACKING

CROSS-REFERENCE TO PRIOR APPLICATIONS

This application is the U.S. National Phase application under 35 U.S.C. § 371 of International Application No. PCT/EP2016/080708, filed on Dec. 13, 2016, which claims the benefit of European Patent Application No. 15201890.9, filed on Dec. 22, 2015. These applications are hereby incorporated by reference herein.

FIELD OF THE INVENTION

The present invention relates to an ultrasound-based system for localizing a medical device within the field of view of an ultrasound imaging probe.

BACKGROUND OF THE INVENTION

Medical devices such as needles, catheters and interventional tools are often difficult to visualize in an ultrasound image due to the specular nature of their reflectivity, particularly at unfavorable incidence angles.

In one solution to this problem, patent application WO2015/101949 discloses a tool navigation system employing an ultrasound probe, an ultrasound scanner, and an interventional tool. The ultrasound scanner generates an ultrasound image corresponding to an acoustic image plane of the ultrasound probe. Ultrasound transmitters and receivers that are attached to the interventional tool and to the ultrasound probe are used to track the position of the interventional tool relative to the acoustic image plane.

A drawback of known localization systems in which tracking is provided by different transducers to those of the ultrasound probe, is the need to calibrate the coordinate system of the tracking system to the field of view of the ultrasound probe. Conventionally this is performed in a factory-based calibration step.

A document entitled "Time of Flight and FMCW Catheter Localization" by Mung, J, et al; 2009 IEEE International Ultrasonics Symposium Proceedings; 20 Sep. 2009; pp 590-593; discloses a system that uses ultrasound signals to track the 3D location of a catheter.

Document WO98/40760 discloses a system for displaying a 2-D ultrasound image in a 3-D viewing environment. A detachable housing containing position transducers is attached to a conventional 2-D ultrasound imaging head to provide position data of an imaging plane generated by an image transducer.

SUMMARY OF THE INVENTION

In seeking to alleviate the drawbacks of known localization systems, a system for determining the position of an ultrasound detector that is attached to a medical device is provided. The system includes at least three ultrasound emitters and a position triangulation unit. The ultrasound emitters are arranged in a predetermined configuration on a frame that is adapted for attachment to an ultrasound imaging probe. The ultrasound imaging probe has an imaging field of view. The position triangulation unit is configured to communicate with the ultrasound emitters and to cause each ultrasound emitter to emit ultrasound signals. Moreover the position triangulation unit is adapted for receiving, from the ultrasound detector, signals indicative of ultrasound signals detected by the ultrasound detector; and is further configured to determine, by triangulation, a spatial position of the ultrasound detector relative to the ultrasound emitters based on a first set of time delays between the emission of an ultrasound signal by each of the ultrasound emitters and its detection by the ultrasound detector. The frame includes a detachable reference volume comprising a background volume and at least one inclusion or void. The at least one inclusion or void has an ultrasound acoustic impedance that differs from the ultrasound acoustic impedance of the background volume. Moreover, when the detachable reference volume is attached to the frame and the frame is attached to the ultrasound imaging probe, the at least one inclusion or void is configured to provides a corresponding at least one image feature within the field of view of the ultrasound imaging probe.

In so doing, an add-on frame for an ultrasound imaging probe is provided which can be used to track the position of an ultrasound detector that is attached to a medical device. The tracking facility alleviates the issue of poor visibility suffered by many medical devices under ultrasound. When the detachable reference volume is attached to the frame and the frame is attached to the ultrasound imaging probe, the image feature can be used to calibrate the coordinate system of the tracking system to the field of view of the ultrasound probe. This is because the at least one inclusion or void is at a predetermined position with respect to the at least three emitters, and the inclusion or void is visible via the image feature in the ultrasound image. The detachable reference volume can subsequently be detached and the medical device can be tracked with respect to the ultrasound imaging probe.

In accordance with another aspect of the invention the field of view of the ultrasound imaging probe extends along a depth axis away from the ultrasound imaging probe and the at least one inclusion or void is in the form of an elongate shape. Moreover the elongate shape extends transversely with respect to the depth axis. The elongate shape provides a feature at a predetermined distance from the ultrasound emitters along the depth axis and this can be used to map the coordinate system of the tracking system to the field of view of the ultrasound probe along the depth axis. Furthermore, because the elongate shape extends transversely with respect to the depth axis, the rotation of the feature as seen in the ultrasound image can be used to map the coordinate system of the tracking system to the field of view of the ultrasound probe with respect to rotation about the depth axis.

In accordance with another aspect of the invention the detachable reference volume has two or more elongate inclusions or voids that are separated axially along the depth axis. Moreover the elongate inclusions or voids each extend transversely with respect to the depth axis and are mutually rotated with respect to the depth axis. The plurality of inclusions or voids can be used to map the coordinate system of the tracking system to the field of view of the ultrasound probe with respect to rotation about the depth axis. This aspect of the invention is particularly useful when the field of view of the ultrasound probe is restricted, for example in the form of a plane, when the inclusions or voids may be only partly visible in the planar image due to a large rotational error.

Other aspects of the invention are defined in the independent claims, including a calibration method and a computer program product.

DETAILED DESCRIPTION OF THE INVENTION

In order to illustrate the principles of the present invention, various systems are described in which the tracking of a medical device, exemplified by a needle, is provided by a position triangulation unit and three ultrasound emitters that are attachable to a 2D ultrasound imaging probe. It is however to be appreciated that the invention also finds application in the tracking of other medical devices such as a catheter, a guidewire, a probe, an endoscope, an electrode, a robot, a filter device, a balloon device, a stent, a mitral clip, a left atrial appendage closure device, an aortic valve, a pacemaker, an intravenous line, a drainage line, a surgical tool such as a tissue sealing device or a tissue cutting device. It is also to be appreciated that the invention finds application with other types of ultrasound imaging probes such as a 3D imaging probe, a transesophageal probe (TEE), transthoracic probe (TTE), transnasal probe (TNE), intracardiac probe (ICE), intravascular probe (IVUS).

Figure 1:
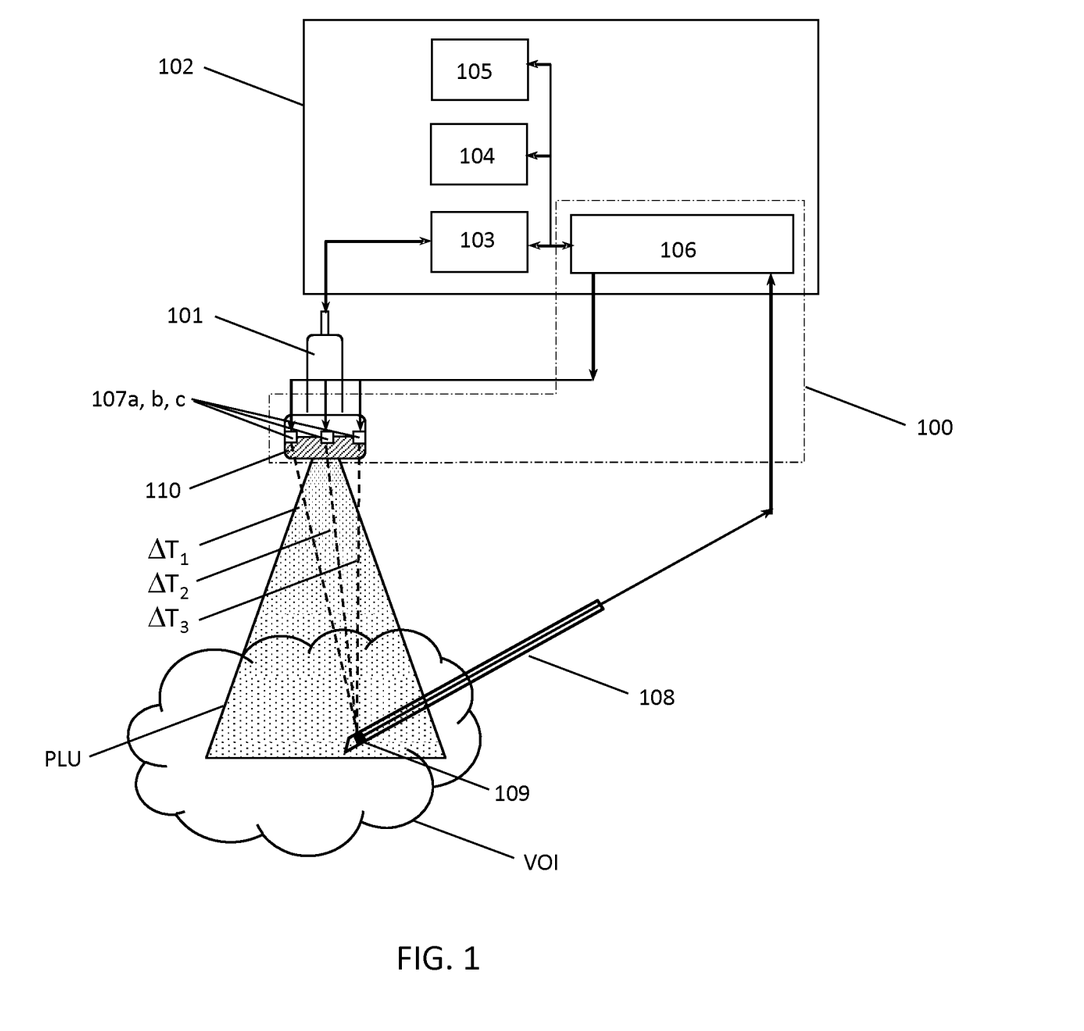
FIG. 1 illustrates a conventional ultrasound imaging system in combination with a localization system 100.

FIG. 1 illustrates a conventional ultrasound imaging system in combination with a localization system 100. The conventional ultrasound imaging system in FIG. 1 includes ultrasound imaging probe 101, imaging system processor 103, imaging system interface 104 and display 105. Imaging system processor 103, imaging system interface 104 and display 105 are located within console 102. Console 102 may be used to supervise a medical procedure. Ultrasound imaging probe 101 is attached to console 102 by means of a cable as indicated by the connecting arrow. Ultrasound imaging probe 101 includes a one or two-dimensional array of ultrasound transceivers (not shown) for transmitting and receiving ultrasound energy from a volume of interest VOI. Console 102 may also include electronic driver and receiver circuitry (not shown) that is configured to amplify and/or to adjust the phase of signals transmitted by or received by ultrasound imaging probe 101, or received by ultrasound detector 109. The electronic driver and receiver circuitry may be used to steer the emitted and/or received ultrasound beam direction. The transceiver array may thus be used to generate either a 2D ultrasound image as indicated by imaging plane PLU, or a 3D ultrasound image. Console 102 may also include a memory (not shown) for storing programs and applications. The memory may for example store ultrasound beam control software that is configured to control the sequence of ultrasound signals transmitted by and/or received by ultrasound imaging probe 101. It is to be noted however that whilst some of the ultrasound imaging system items are described above as being located within console 102, some of these items may alternatively be located within the imaging system probe, as is the case for example in the Philips LUMIFY ultrasound imaging system.

Localization system 100, that comprises three ultrasound emitters 107a, b, c, arranged on a frame 110, and position triangulation unit 106 is also included FIG. 1. Localization system 100 may be used to determine the position of a medical device such as exemplary medical needle 108 having ultrasound detector 109 attached thereto.

Ultrasound detector 109 in FIG. 1 may for example be made from a piezoelectric material. Preferably the ultrasound detector is made from a Polyvinylidene fluoride material, i.e. PVDF, or one of the related materials in the PVDF group that include PVDF co-polymers and PVDF ter-polymers, although other materials are also suitable. Such materials are available in the form of a thin film and are therefore particularly suited to attachment to a medical device, as described in patent application PCT/IB2015/052425, published as WO2015/155645. Ultrasound detector 109 is preferably adapted for attachment to a medical device using an adhesive layer. A snap-fit connector, or a compression fitting connector that mates with a corresponding connector on the medical device may alternatively be used.

The three ultrasound emitters 107a, b, c in FIG. 1 are arranged in a predetermined, spaced-apart, configuration on frame 110 that is adapted for attachment to ultrasound imaging probe 101. The frame may be attached to ultrasound imaging probe 101 by various means including a press-fit connection, a snap fit connection, an elastic strap or using an adhesive. In a preferred arrangement the ultrasound emitters 107a, b, c lie in a common plane and are held by the frame alongside the imaging probe. Alternatively the emitters may be arranged to lie along a straight line. Ultrasound emitters 107a, b, c may be made from conventional materials such as piezoelectric materials that expand or contract upon application of electrical pulses and thereby emit ultrasound signals. Preferably the ultrasound emitters are omnidirectional emitters. However, directional or focused emitters that emit ultrasound waves into a cone angle of less than $4\pi$ steradians may also be used.

In localization system 100, position triangulation unit 106 communicates with the three ultrasound emitters 107a, b, c as illustrated by the interconnecting arrows and is configured to cause each ultrasound emitter to emit ultrasound signals.

Preferably position triangulation unit 106 is connected to the three ultrasound emitters with electrical wire(s), although wireless communication, for example using an optical, infrared, or an RF communication link is also contemplated. Moreover, the ultrasound signals emitted by the ultrasound emitters may include a single pulse or multiple pulses. In principle the use of a single pulse is adequate to allow the position triangulation unit to determine a set of time delays that are used to triangulate the position of the ultrasound detector. Multiple pulses may alternatively be used to improve their detected signal to noise ratio or to improve their discrimination. In either case the pulses may be emitted sequentially or simultaneously by the emitters. When emitted simultaneously, coding may be used to permit ultrasound detector 109 to distinguish between the pulses emitted by each emitter. Such coding may take the form of different pulse durations, different pulse frequencies, or different pulse sequences. Moreover, when multiple pulses are used, preferably the frequency of pulses emitted by each ultrasound emitter is different to, for example at least twice, or at most half of the pulse frequency of the ultrasound imaging system. Preferably the ultrasound signals emitted by each of the three ultrasound emitters comprise a frequency of 1 MHz or less. This is significantly less than the approximately 2-10 MHz frequencies emitted by a conventional ultrasound imaging system. By separating the frequencies used by the ultrasound emitters from those used by the ultrasound transceiver array in the ultrasound imaging system, interference between the two systems is reduced. It is also contemplated to interleave the emission of pulses from the three emitters between consecutive frames of the ultrasound imaging system in order to reduce interference between the two systems.

In localization system 100, position triangulation unit 106 is adapted to receive, from ultrasound detector 109, signals indicative of ultrasound signals detected by the ultrasound detector; and is further configured to determine, by triangulation, a spatial position of the ultrasound detector 109 relative to the at least three ultrasound emitters 107a, b, c, based on a first set of time delays $\Delta T_1$, $\Delta T_2$, $\Delta T_3$ between the emission of an ultrasound signal by each of the at least three ultrasound emitters 107a, b, c and its detection by the ultrasound detector 109.

Position triangulation unit 106 may for example have an electrical input that is suitable for receiving such signals from ultrasound detector 109. The input may for example be a wired input as indicated by the connecting arrows in FIG. 1. Alternatively it is also contemplated to use a wireless input wherein a communication path is provided by an optical, infrared, or an RF communication link. In either case the position triangulation unit may also include analogue to digital conversion electronics (not shown in FIG. 1) for interfacing with ultrasound detector 109.

The time delays $\Delta T_1$, $\Delta T_2$, $\Delta T_3$ used by position triangulation unit 106 to triangulate the detector position may be computed using a timer, for example. The timer might be triggered to start counting at a position on the emitted ultrasound emitter signal and triggered to stop counting by a corresponding position on the detected emitter signal. Alternatively the time delays may be computed by correlating the detected ultrasound signal with the emitted ultrasound signal. Other techniques, including the use of matched filtering are also suitable for this purpose. Any of these techniques may be implemented by a processor, for example in position triangulation unit 106, or by dedicated electronic circuitry.

Figure 2:
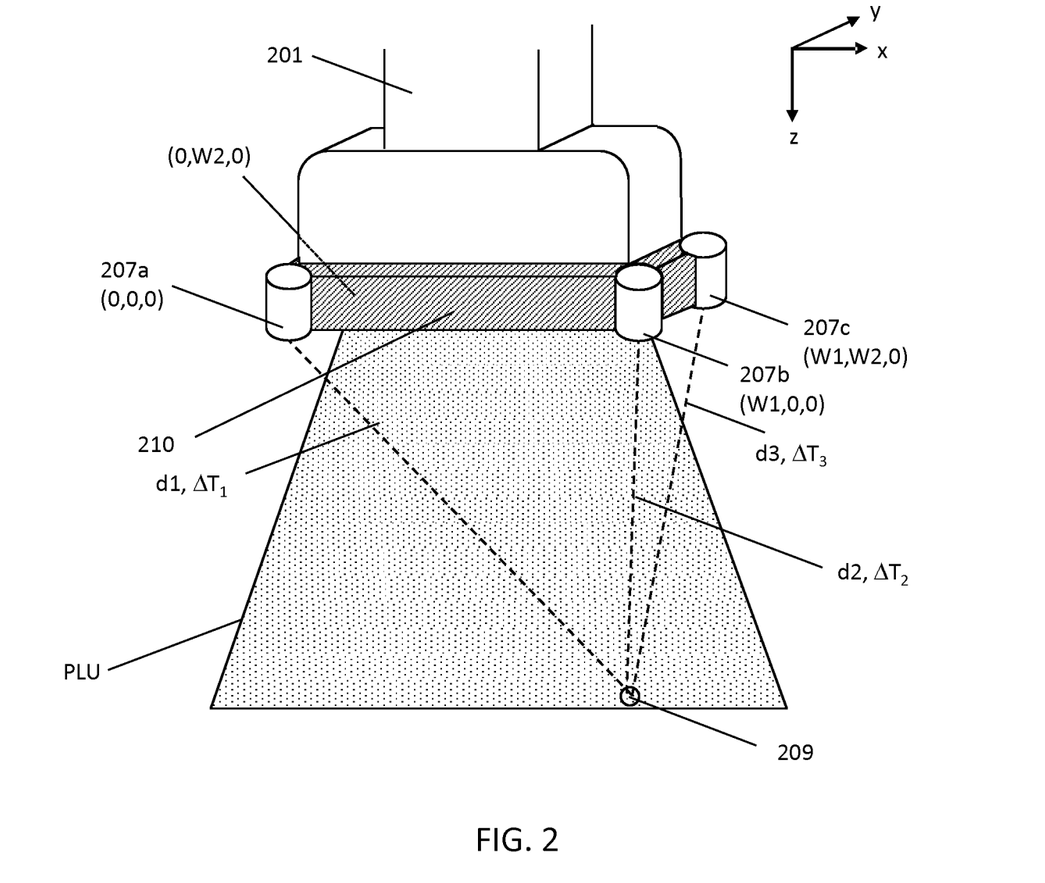
FIG. 2 illustrates an ultrasound probe 201 together with three ultrasound emitters 207a, b, c attached thereto by means of frame 210, together with an ultrasound detector 209.

An exemplary triangulation calculation that may be performed by position triangulation unit 106 is illustrated with reference to FIG. 2. FIG. 2 illustrates an ultrasound probe 201 together with three ultrasound emitters 207a, b, c attached thereto by means of frame 210, together with an ultrasound detector 209. Imaging plane PLU of ultrasound imaging probe 201 is also shown in FIG. 2. In FIG. 2 three ultrasound emitters 207a, b, c are located in Cartesian coordinate (x,y,z) positions (0,0,0), (W1,0,0) and (W1,W2, 0). The time delays $\Delta T_1$, $\Delta T_2$ and $\Delta T_3$, of ultrasound wave propagation between respective emitters 207a, b, c and ultrasound detector 209 correspond to the lengths of vertices d1, d2, d3 that extend from a plane that is defined by the positions of the three ultrasound emitters. The lengths of vertices d1, d2, d3 can be calculated using the speed of ultrasound wave propagation in the propagation medium. Subsequently, using triangulation the position of detector 209 can be determined in Cartesian coordinate space using Equations 1-3 below, in which W1 and W2 represent the relative positions of the emitters as shown in FIG. 2.

$$S_x = \frac{W_1^2 + d_1^2 - d_3^2}{2W_1} \quad \text{Equation 1}$$

$$S_y = \frac{W_2^2 + d_1^2 - d_2^2}{2W_2} \quad \text{Equation 2}$$

$$S_z = \sqrt{d_1^2 - S_x^2 - S_y^2} \quad \text{Equation 3}$$

Thus, using equations 1-3, the position of detector 209 relative to the three ultrasound emitters 207a, b, c can be determined by triangulation. Additional emitters not shown in FIG. 2 or FIG. 1 may also be used, for example at position (0,W2,0), in order to improve the accuracy of the triangulation calculation, or to provide redundancy in case one of the signal paths d1, d2, d3 is obscured.

Figure 3A:
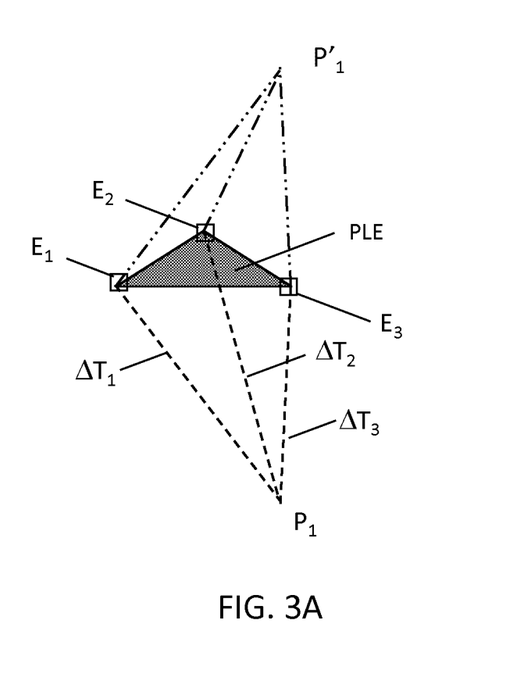
FIG. 3A illustrates three ultrasound emitters $E_1$, $E_2$, $E_3$ that are arranged in a planar configuration.
Figure 3B:
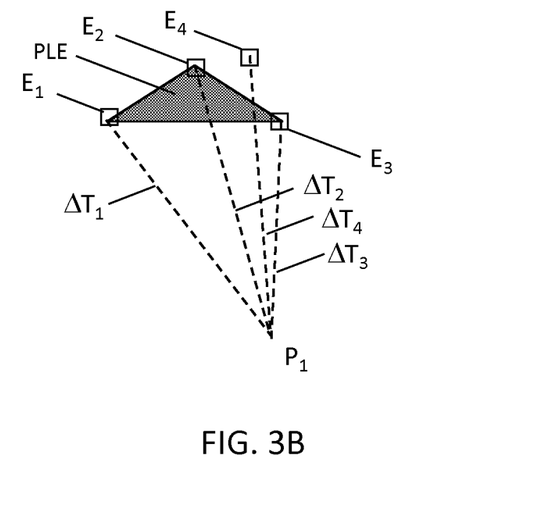
FIG. 3B illustrates three ultrasound emitters $E_1$, $E_2$, $E_3$ that are arranged in a planar configuration and one ultrasound emitter $E_4$ that lies beyond this plane.
Figure 3C:
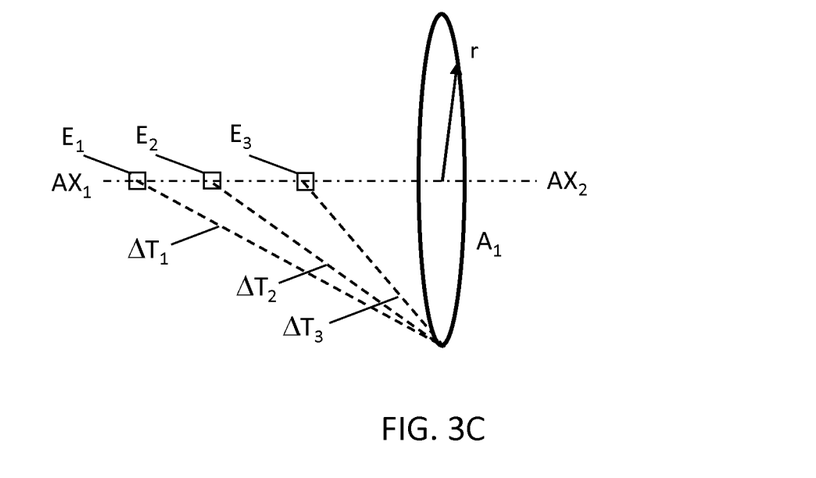
FIG. 3C illustrates three ultrasound emitters $E_1$, $E_2$, $E_3$ that are arranged along a straight line $AX_1$-$AX_2$.

In order to further illustrate operation of position determination unit 106, FIG. 3A illustrates three ultrasound emitters $E_1$, $E_2$, $E_3$ that are arranged in a planar configuration, FIG. 3B illustrates three ultrasound emitters $E_1$, $E_2$, $E_3$ that are arranged in a planar configuration and one ultrasound emitter $E_4$ that lies beyond this plane, and FIG. 3C illustrates three ultrasound emitters $E_1$, $E_2$, $E_3$ that are arranged along a straight line $AX_1$-$AX_2$. As described above in relation to FIG. 2, the minimum number of ultrasound emitters that is required to perform the desired triangulation, is three. However, various arrangements of these emitters is possible, which is illustrated in FIG. 3. Preferably the ultrasound emitters are arranged in a planar configuration, as indicated by the shaded portion of FIG. 3A that joins the emitters, emitter plane PLE. This arrangement improves the tracking of the detector $D_1$ because the detector's position can be localized to point $P_1$ based on the time delays $\Delta T_1$, $\Delta T_2$, $\Delta T_3$. Point $P_1'$ that also satisfies the triangulation calculations can be ruled-out simply with knowledge of which side of the emitter plane the detector lies. In the medical environment contemplated, point $P_1'$ can be ruled out since the detector is unlikely to be positioned behind the ultrasound imaging probe. It is also contemplated to use more than three ultrasound emitters in the system of FIG. 1. Such redundancy enhances the spatial positioning accuracy of the ultrasound detector when signals from the additional detectors are detected. The redundancy provided by the additional emitters can also facilitate more reliable operation, for example in the event of a weak or obstructed signal from one of the emitters, providing signals from the remaining three emitters are detected. As compared to FIG. 3A, the arrangement in FIG. 3B includes an out-of-plane emitter $E_4$. The out-of-plane emitter $E_4$ can be used either to provide the above-described redundancy, and additionally provides an indication of which side of the shaded plane, emitter plane PLE, the detector lies, thereby eliminating the point $P_1'$ solution shown in FIG. 3A. The arrangement in FIG. 3C illustrates that a linear arrangement of three emitters along straight line $AX_1$-$AX_2$ can be used to localize the position of the detector to an arc $A_1$ of a circle having radius r about axis $AX_1$-$AX_2$. Whilst this does not localize the detector position to a particular point, the ability to localize the detector to a position along an arc is still of use in narrowing-down its location. When used with an ultrasound imaging probe that has an imaging plane, preferably the straight line along which the emitters are arranged does not lie in the ultrasound imaging plane.

Returning to FIG. 1, whilst position triangulation unit 106 is shown as being within console 102, this may alternatively be located together with ultrasound emitters 107a, b, c. In other words, localization system 100 may alternatively comprise a single unit. In this case both the three ultrasound emitters and position triangulation unit 106 are adapted for attachment to ultrasound imaging probe 101. This reduces the form factor of localization system 100.

Thus, in use, localization system 100 may be used to determine the position of exemplary medical device 108 with respect to the coordinate system of ultrasound emitters 107*a, b, c* when ultrasound detector 109 is attached thereto.

Figure 4:
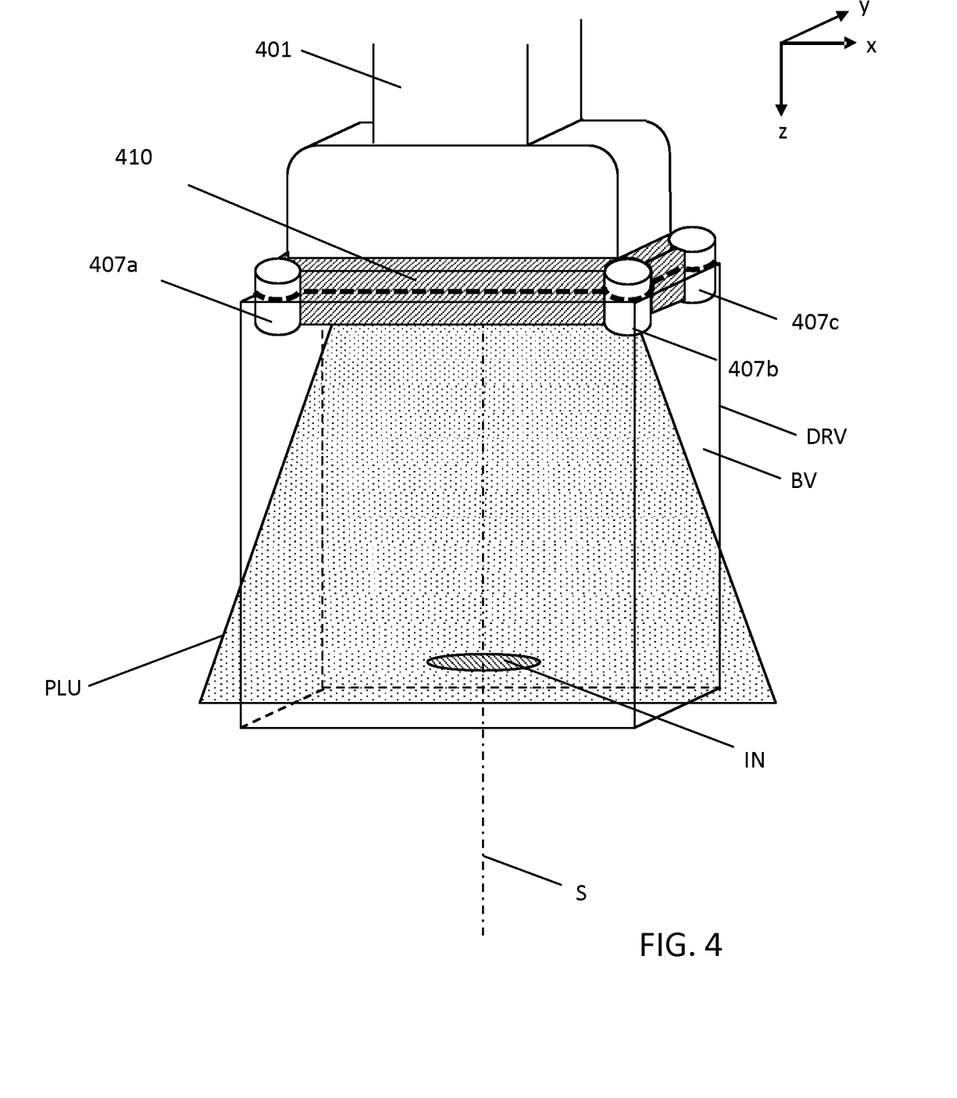
FIG. 4 illustrates an ultrasound probe 401 together with three ultrasound emitters 407a, b, c attached thereto by means of frame 410, together with a detachable reference volume DRV that comprises a background volume BV and an inclusion or void IN that is within the field of view PLU of the ultrasound imaging probe 401.

In order to map the coordinate system of the localization system 100 to the field of view of the ultrasound probe PLU, localization system 100 in FIG. 1 is further provided with a detachable reference volume DRV as illustrated with reference to FIG. 4. FIG. 4 illustrates an ultrasound probe 401 together with three ultrasound emitters 407*a, b, c* attached thereto by means of frame 410, together with a detachable reference volume DRV that comprises a background volume BV and an inclusion or void IN that is within the field of view PLU of the ultrasound imaging probe 401. Detachable reference volume DRV is detachable from frame 410 along the thick dashed lines, i.e. a coupling interface as illustrated in FIG. 4, thus providing the arrangements in FIG. 1, FIG. 2 and FIG. 5 in which the detachable reference volume DRV is detached from frame 110, 210, 510 respectively. Optionally the coupling interface may include at least one mechanical registration feature for attaching the detachable reference volume DRV to the frame 110, 410, 510 in a predetermined orientation. The mechanical registration feature may be for example a dowel that is attached to the detachable reference volume, and which mates with a corresponding hole in the frame. The dowel and the hole may for example have a particular cross section such as a star in order to ensure that the detachable reference volume and the frame can couple only in one orientation. A plurality of such dowels may also be used, which case each dowel may have e.g. a circular cross section. Moreover, other mechanical registration features are also suitable for this purpose, including a groove that mates with a ridge, or a male plug that mates with a female socket. Temporary coupling across the coupling interface may also be facilitated using for example a magnet or a strap at the coupling interface. Preferably the predetermined orientation is such that when the detachable reference volume DRV is attached to the frame and the frame is attached to the ultrasound imaging probe, the at least one inclusion or void is configured to provide a corresponding at least one image feature within the field of view PLU of the ultrasound imaging probe. Detachable reference volume DRV may be included within a container, for example. Inclusion or void IN has an ultrasound acoustic impedance that differs from the ultrasound acoustic impedance of the background volume BV. Preferably the at least one inclusion or void IN has an ultrasound acoustic impedance that differs by at least 5%, or at least 10% or at least 15% from the ultrasound acoustic impedance of the background volume. Thus, when detachable reference volume DRV is attached to frame 410 and the frame 410 is attached to ultrasound imaging probe 401, the inclusion or void is configured to provide a corresponding image feature within the field of view PLU of the ultrasound imaging probe. Multiple inclusions or voids may be added to FIG. 4 in the same way to provide more discernible image features. Detachable reference volume DRV may be subsequently removed after the mapping procedure has taken place so as to avoid interfering with the usual imaging operation of ultrasound imaging probe 101. Background volume BV is preferably a material having a similar acoustic impedance to skin, i.e. $1.7 \times 10^6$ kg $m^{-2} s^{-1}$ in order to most closely mimic its usage environment and to avoid excessive ultrasound reflections back to the ultrasound transducers and ultrasound emitters. One suitable material for background volume BV is Zerdine, supplied by CIRS of Virginia, US and disclosed in U.S. Pat. No. 5,196,343. Alternatively this may be provided by water, gelatin, or ultrasound matching gel. Suitable materials for inclusion IN include nylon or urethane rubber, or other polymers. Moreover when a void is used this may be filled with a fluid or gas such as air or nitrogen. Inclusion or void IN may be in the form of various shapes, although in principle a single point is sufficient to calibrate the range of the localization system 100 to the range in the field of view of the ultrasound probe PLU.

Elongated shapes are preferred for inclusion or void IN because these offer the additional possibility of determining the relative rotation between the coordinate system of the tracking system and that of the field of view of the ultrasound probe PLU. In one embodiment the field of view PLU of the ultrasound imaging probe 401 extends along a depth axis S in FIG. 4 away from ultrasound imaging probe 401, and the inclusion or void IN is in the form of an elongate shape that extends transversely with respect to the depth axis S. Other shapes are also suitable, such as a cross or a star or a t-shape.

In another embodiment the inclusion or void has a dimension of at least 1 mm in a transverse direction to the depth axis S. This provides a more easily discernible image feature in an ultrasound image.

In another embodiment there are two or more elongate inclusions or voids that are separated axially along the depth axis S. Moreover, the two or more elongate inclusions or voids each extend transversely with respect to the depth axis and are mutually rotated with respect to the depth axis. The two or more inclusions or voids can be used to calibrate the coordinate system of the tracking system to the field of view of the ultrasound probe with respect to rotation about the depth axis. This aspect of the invention is particularly useful when the field of view of the ultrasound probe is restricted, for example in the form of a plane, when the inclusions or voids may be only partly visible in the planar image due to a large rotational error. The relative rotation between the coordinate system of the localization system 100 and the field of view of the ultrasound probe PLU may for example be determined by measuring the relative lengths of each inclusion or void in the field of view of the ultrasound imaging probe.

Figure 5:
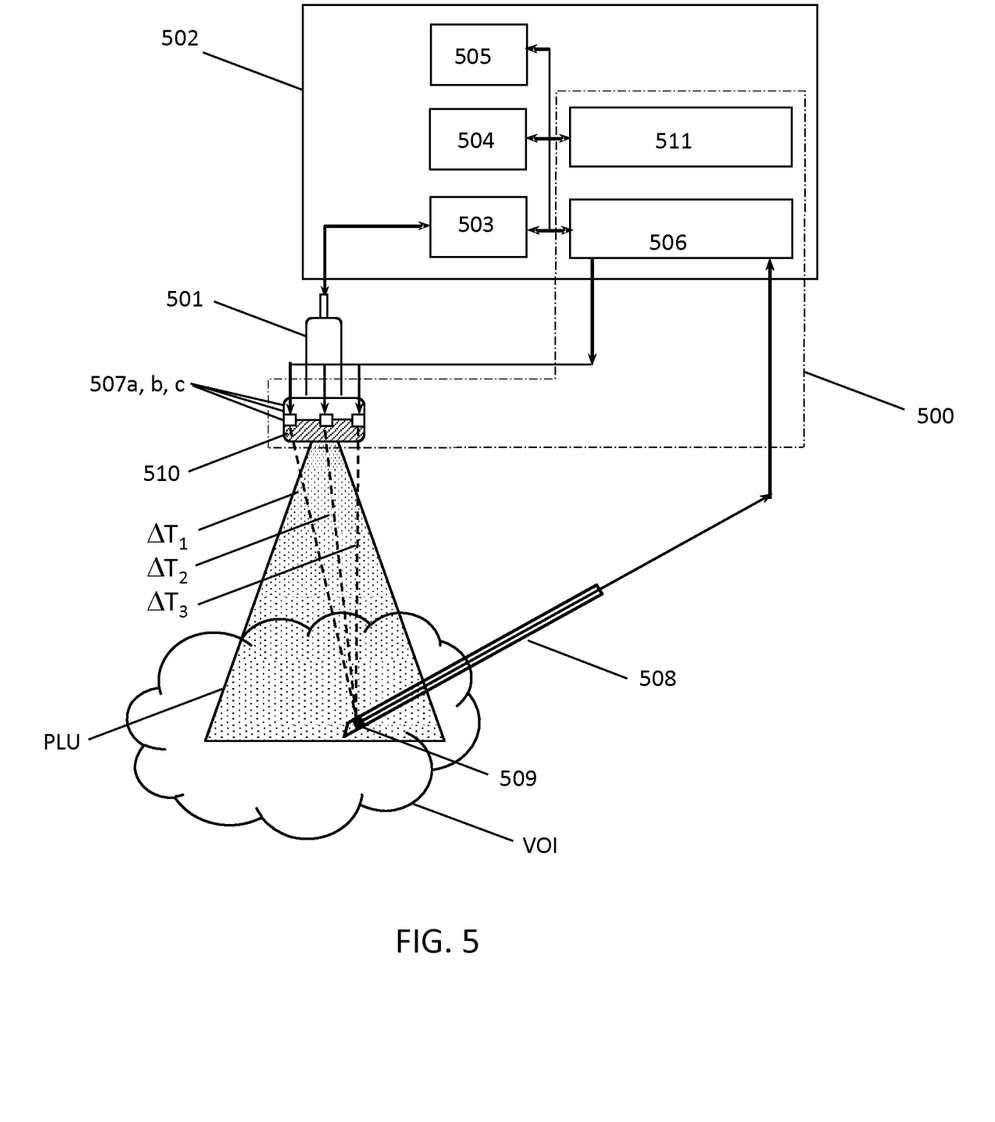
FIG. 5 illustrates a conventional ultrasound imaging system in combination with a localization system 500.

FIG. 5 illustrates a conventional ultrasound imaging system in combination with a localization system 500. In addition to the corresponding elements of FIG. 1, FIG. 5 includes image fusion unit 511. The conventional ultrasound imaging system in FIG. 5 includes ultrasound imaging probe 501, imaging system processor 503, imaging system interface 504 and display 505. Imaging system processor 503, imaging system interface 504 and display 505 are located within console 502. Ultrasound imaging probe 501 includes a one or two-dimensional array of ultrasound transceivers (not shown) for transmitting and receiving ultrasound energy from a volume of interest VOI. Console 502 may also include electronic driver and receiver circuitry (not shown) that is configured to amplify and/or to adjust the phase of signals transmitted by or received by ultrasound imaging probe 501, or received by ultrasound detector 509. The electronic driver and receiver circuitry may be used to steer the emitted and/or received ultrasound beam direction. The transceiver array may thus be used to generate either a 2D ultrasound image as indicated by imaging plane PLU, or a 3D ultrasound image. Console 502 may also include a memory (not shown) for storing programs and applications.

A localization system 500, that comprises three ultrasound emitters 507a, b, c, arranged on a frame 510, and position triangulation unit 506 is also included FIG. 5. Localization system 500 may be used to determine the position of a medical device such as exemplary medical needle 508 having ultrasound detector 509 attached thereto.

In comparison to FIG. 1, additional image fusion unit 511 in FIG. 5 is in communication with imaging system processor 503 and position triangulation unit 506. Image fusion unit 511 is configured to generate a fused image representation based on the ultrasound image representation and the spatial position of the ultrasound detector. Techniques for providing the fused image representation are well known in the image processing field. Image fusion unit 511 may comprise one or more processors that perform the desired image fusion. The image fusion may alternatively be carried out by imaging system processor 503, or the same processor that performs the function of position triangulation unit 506. The spatial position of the ultrasound detector may for example be indicated by a marker such as a cross, a circle, a crosshair, an arrow, a pointer or indeed a change in color of the ultrasound image. The fused image may also be provided in the form of a partially-transparent marker which allows viewing of the portion of ultrasound image underneath it. When the detector is attached to a medical device the indication of the spatial position of the ultrasound detector may be replaced by a position of a point on the medical device.

When the image generated by imaging system processor 503 is a 2D ultrasound image, it is also contemplated to indicate, in the 2D ultrasound image, which side of the ultrasound image plane the ultrasound detector lies. This is particularly useful when the detector lies beyond the ultrasound image plane, i.e. it lies "out-of-plane", because it alerts a physician to tilt the ultrasound image probe in order to bring the detector back into the ultrasound image plane, i.e. "in-plane". In so doing the physician can visualize the exact position of the detector with respect to the ultrasound image. In this arrangement, in localization system 500 illustrated in FIG. 5, imaging system processor 503 is configured to reconstruct an ultrasound image representation of a plane PLU that intersects a volume of interest VOI. Furthermore, position triangulation unit 506 is configured to provide, in the fused image, an indication of the side of the plane on which the ultrasound detector is located when the ultrasound detector lies beyond the plane of the ultrasound image representation. This is possible with the arrangement in FIG. 5 because localization system 500 is not limited to in-plane tracking of the position of detector 509, and thus the actual detector position in relation to plane PLU is readily determined. Such an indication of the side of the plane on which the ultrasound detector is located may take the form of a textual indication in the fused image, for example "above plane" or "below plane", an arrow showing the direction in which the probe must be tilted in order to bring the ultrasound detector back in-plane, or a distance between the ultrasound detector and the plane; preferably the shortest distance to the plane. It is also contemplated to provide the indication in the form of a marker, such as a circle or a cross, at a point in the 2D ultrasound image that is nearest to the ultrasound detector, wherein the marker has a size that varies in accordance with the out-of-plane distance to the ultrasound detector.

In another embodiment a second ultrasound detector may also be attached to the medical device 108, 508 of FIG. 1 or FIG. 5. In this, the position triangulation unit 106, 506 is further adapted for receiving, from the second ultrasound detector, signals indicative of ultrasound signals detected by the second ultrasound detector. Moreover the position triangulation unit is configured to determine, by triangulation, a spatial position of the second ultrasound detector relative to the at least three ultrasound emitters 107a, b, c, 507a, b, c based on a second set of time delays $\Delta T_{21}$, $\Delta T_{22}$, $\Delta T_{23}$ between the emission of an ultrasound signal by each of the at least three ultrasound emitters and its detection by the second ultrasound detector. Furthermore, the position triangulation unit 106, 506 is further configured to determine a trajectory between the ultrasound detector 109, 509 and the second ultrasound detector based on the spatial positions of the ultrasound detector and the second ultrasound detector. In this embodiment the relative positions of the two ultrasound detectors inherently define a trajectory. When the detectors are attached to a medical device, this trajectory may thus be used to indicate a trajectory of the medical device. This embodiment finds particular application in medical devices such as needles that have an axis, and where it is valuable to determine the trajectory of that axis. This may subsequently be indicated in an ultrasound image generated by the image fusion unit. In medical procedures using a needle it is valuable to know the needle trajectory in order to determine whether insertion of the needle at its present position will result in the needle tip position ending-up at a desired point in a volume of interest.

In another embodiment a calibration method is disclosed that may be used with the system in FIG. 1 or FIG. 5. It may also be used in combination with the other embodiments described herein. The calibration method may be used to calibrate the coordinate system of the tracking system to the field of view of the ultrasound probe. The mapping may also be used to determine the position of the detector 109, 509, with respect to the field of view PLU of the ultrasound probe 101, 501. In general the ultrasound probe has a field of view that is defined by a coordinate system, and ultrasound image features are mapped into this field of view or coordinate system by the ultrasound image reconstruction process. With reference to FIG. 1 and FIG. 5, the tracking system likewise has a coordinate system which is defined in relation to the positions of its ultrasound emitters 107a, b, c, 507a, b, c. One method of aligning the two coordinate systems could be to ensure that the ultrasound emitters are in an exact position in relation to the ultrasound transceiver array. However in general such an alignment is tricky to achieve, particularly when the frame is retro-fitted to an ultrasound probe that is already in service in the field. This may thus result in a rotational or a range error in the detector position as determined by the position triangulation unit. The calibration method of this embodiment provides a mapping that accounts for such misalignments.

The calibration method includes the steps of: i) providing a measured ultrasound image representation corresponding to the field of view PLU of the ultrasound imaging probe 501 based on ultrasound signals transmitted and received by the ultrasound imaging probe 501, and wherein the measured ultrasound image representation includes at least a portion of the at least one image feature; ii) providing a predicted ultrasound image representation corresponding to a predicted field of view PLU of the ultrasound imaging probe 501 based on a position of the at least one inclusion or void IN in relation to the at least three ultrasound emitters 107a, b, c, 507a, b, c; and iii) determining a translation between the predicted ultrasound image representation and the measured ultrasound image representation for mapping the spatial position of the ultrasound detector 109, 509 as determined by the position triangulation unit 106, 506 to the field of view PLU of the ultrasound imaging probe 501.

The predicted ultrasound image representation includes at least part of the image feature corresponding to the inclusion or void IN, and is the image that would be generated by the ultrasound imaging system when the frame, i.e. ultrasound emitters, is positioned respective the transceiver array, i.e. the ultrasound imaging probe, such that the coordinate system of the ultrasound imaging probe is aligned with the coordinate system of the tracking system. In other words, the predicted ultrasound image representation corresponds to the field of view, including part of the inclusion, when the coordinate systems are aligned.

Various known techniques from the field of image mapping can be used to provide the desired translation between the predicted and measured ultrasound image representations. The mapping may include operations such as rotation, scaling, translation, and other affine transformations.

Having determined the mapping that is necessary to map the measured to the predicted image representation, this mapping can be applied to each point within the coordinate system of the tracking system in order to align measured positions in the coordinate system of the tracking system to measured positions in the field of view of the ultrasound imaging probe.

In another embodiment a computer program product is disclosed. The computer program product comprises instructions which when executed on a processor cause the processor to carry out the calibration method steps described above. The computer program product may be provided by dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor "DSP" hardware, read only memory "ROM" for storing software, random access memory "RAM", non-volatile storage, etc. Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system, or apparatus or device, or a propagation medium. Examples of a computer-readable medium include a semiconductor or solid state memory, magnetic tape, a removable computer diskette, a random access memory "RAM", a read-only memory "ROM", a rigid magnetic disk and an optical disk. Current examples of optical disks include compact disk-read only memory "CD-ROM", compact disk-read/write "CD-R/W", Blu-Ray™ and DVD.

The invention claimed is:

1. A system for determining a position of an ultrasound detector, the system comprising:
  a medical device with an ultrasound detector attached to the medical device;
  a frame configured to attach to an ultrasound imaging probe having a field of view defined by a coordinate system, the frame comprising:
    at least three ultrasound emitters arranged in a predetermined configuration on the frame, and
    a detachable reference volume that includes a background volume and at least one inclusion or void, the at least one inclusion or void having an ultrasound acoustic impedance that differs from the ultrasound acoustic impedance of the background volume such that, when the detachable reference volume is attached to the frame and the frame is attached to the ultrasound imaging probe, the at least one inclusion or void is configured to provide a corresponding at least one image feature within the field of view of the ultrasound imaging probe; and
  a position triangulation processor configured to:
    communicate with the at least three ultrasound emitters and to cause each ultrasound emitter to emit ultrasound signals,
    receive, from the ultrasound detector, signals indicative of the ultrasound signals being detected by the ultrasound detector,
    determine, by triangulation, a spatial position of the ultrasound detector attached to the medical device in a coordinate system defined in relation to the at least three ultrasound emitters based on a first set of time delays between emission of an ultrasound signal by each of the at least three ultrasound emitters and detection of the ultrasound signal by the ultrasound detector, and
    determine the spatial position of the ultrasound detector within the field of view of the ultrasound imaging probe based on mapping the coordinate system of the at least three ultrasound emitters to the coordinate system of the ultrasound imaging probe using the at least one image feature provided by the at least one inclusion or void,
    wherein the position triangulation processor is configured to determine the spatial position of the ultrasound detector using the at least three ultrasound emitters and the at least one inclusion or void during a medical procedure.

2. The system according to claim 1, wherein the detachable reference volume is detachable from the frame at a coupling interface, and wherein said coupling interface includes at least one mechanical registration feature for attaching the detachable reference volume to the frame in a predetermined orientation.

3. The system according to claim 1, wherein the field of view of the ultrasound imaging probe extends along a depth axis away from the ultrasound imaging probe.

4. The system according to claim 3, wherein the at least one inclusion or void is in the form of an elongated shape, and wherein the elongated shape extends transversely with respect to the depth axis.

5. The system according to claim 3, wherein the at least one inclusion or void has a dimension of at least 1 mm in a transverse direction to the depth axis.

6. The system according to claim 1, wherein the at least one inclusion or void comprises two or more elongated inclusions or voids that are separated axially along a depth axis, and wherein the two or more elongated inclusions or voids each extend transversely with respect to the depth axis and are mutually rotated with respect to the depth axis.

7. The system according to claim 6, wherein the ultrasound acoustic impedance differs by at least 5% from the ultrasound acoustic impedance of the background volume.

8. The system according to claim 7, wherein the ultrasound imaging probe is selected from the group consisting of: a 2D imaging probe, a 3D imaging probe, a transesophageal probe, a transthoracic probe, a transnasal probe, an intracardiac probe, and an intravascular probe.

9. The system according to claim 1, further comprising a second ultrasound detector,
wherein the second ultrasound detector is attached to the medical device,
wherein the position triangulation processor is further configured to:
receive, from the second ultrasound detector, second signals indicative of the ultrasound signals being detected by the second ultrasound detector,
determine, by triangulation, a spatial position of the second ultrasound detector relative to the at least three ultrasound emitters based on a second set of time delays between emission of the ultrasound signal by each of the at least three ultrasound emitters and detection of the ultrasound signal by the second ultrasound detector, and
determine a trajectory between the ultrasound detector and the second ultrasound detector based on spatial positions of the ultrasound detector and the second ultrasound detector.

10. The system according to claim 1, wherein the medical device is selected from the group consisting of:
a needle, a catheter, a guidewire, a probe, an endoscope, an electrode, a robot, a filter device, a balloon device, a stent, a mitral clip, a left atrial appendage closure device, an aortic valve, a pacemaker, an intravenous line, a drainage line, and a surgical tool.

11. The system according to claim 1, wherein the ultrasound imaging probe is configured to transmit and to receive ultrasound energy within the field of view; and
the system further comprising:
an imaging system processor; and
an image fusion processor,
wherein the imaging system processor is in operational communication with the ultrasound imaging probe,
wherein the imaging system processor, the position triangulation processor and the image fusion processor are in mutual communication,
wherein the imaging system processor is configured to reconstruct an ultrasound image representation corresponding to the field of view based on ultrasound signals transmitted and received by the ultrasound imaging probe, and
wherein the image fusion processor is configured to generate a fused image representation based on the ultrasound image representation and the spatial position of the ultrasound detector.

12. The system according to claim 11, wherein the field of view is a plane, and wherein the position triangulation processor is further configured to provide, in the fused image, an indication of a side of a plane on which the ultrasound detector is located when the ultrasound detector lies beyond a plane of the ultrasound image representation.

* * * * *